(12) United States Patent
Springer et al.

(10) Patent No.: US 11,510,548 B2
(45) Date of Patent: Nov. 29, 2022

(54) CAPTURING AN IMAGE OF A SCENE (71) Applicant: Sony Corporation, Tokyo (JP)

(72) Inventors: Paul Springer, Stuttgart (DE); Thimo Emmerich, Stuttgart (DE); Zoltan Facius, Stuttgart (DE)

(73) Assignee: SONY CORPORATION, Tokyo (JP)

( * ) Notice: Subject to any disclaimer, the term of this patent is extended or adjusted under 35 U.S.C. 154(b) by 277 days.

(21) Appl. No.: 16/465,577

(22) PCT Filed: Dec. 14, 2017

(86) PCT No.: PCT/EP2017/082914
§ 371 (c)(1),
(2) Date: May 31, 2019

(87) PCT Pub. No.: WO2018/109117
PCT Pub. Date: Jun. 21, 2018

(65) Prior Publication Data
US 2019/0328209 A1 Oct. 31, 2019

(30) Foreign Application Priority Data
Dec. 16, 2016 (EP) .................... 16204875

(51) Int. Cl.
*A61B 1/00* (2006.01)
*G02B 23/24* (2006.01)

(52) U.S. Cl.
CPC ...... *A61B 1/00009* (2013.01); *A61B 1/00186* (2013.01); *A61B 1/00188* (2013.01); *G02B 23/2484* (2013.01)

(58) Field of Classification Search
CPC ............ A61B 1/00009; A61B 1/00186; A61B 1/00188; A61B 1/045; G02B 23/2484;
(Continued)

(56) References Cited

U.S. PATENT DOCUMENTS 6,984,206 B2   1/2006  Kumei et al.
8,014,069 B2   9/2011  Spilman et al.
(Continued)

FOREIGN PATENT DOCUMENTS

CN   101750736 B   10/2013
JP     9-15535 A    1/1997
(Continued)

OTHER PUBLICATIONS

Office Action dated Sep. 15, 2020, in corresponding Japanese patent Application No. 2019-532767, 6 pages.
(Continued)

*Primary Examiner* — Michael J Carey
*Assistant Examiner* — Christen A. Sharpless
(74) *Attorney, Agent, or Firm* — Xsensus LLP (57) ABSTRACT

An imaging device for use with an endoscope, the imaging device comprising: a lens arrangement operable to receive light from a scene captured by the endoscope and to form an image of the scene using the received light; an image sensor operable to capture the image of the scene formed by the lens arrangement; a birefringent device positioned along an optical path between the endoscope and the image sensor, wherein the birefringent device comprises birefringent material arranged in a plurality of concentric rings, and wherein the birefringent material of each of the concentric rings is configured such that the polarisation directions of an ordinary ray and an extraordinary ray of light from the scene which travels through the birefringent material are different for at least two of the plurality of concentric rings; and an image processor operable to process the captured image to generate an output image.

17 Claims, 8 Drawing Sheets

(58) Field of Classification Search
CPC ... G02B 27/0075; G02B 27/28; G02B 5/3083
USPC .......................................................... 600/109
See application file for complete search history.

(56) References Cited

U.S. PATENT DOCUMENTS

| | | | |
|---|---|---|---|
| 8,047,985 B2 | 11/2011 | Harris | |
| 2004/0105025 A1* | 6/2004 | Scherling | H04N 1/00241 348/335 |
| 2012/0281081 A1* | 11/2012 | Atif | H04N 5/35721 348/E5.09 |
| 2012/0281280 A1* | 11/2012 | Buehler | G02F 1/13363 977/932 |
| 2014/0039259 A1* | 2/2014 | Okaniwa | G02B 23/2476 600/139 |
| 2014/0313498 A1* | 10/2014 | Saenger | G02B 5/3083 355/67 |
| 2016/0291230 A1 | 10/2016 | Weichelt et al. | |
| 2018/0024347 A1* | 1/2018 | Kiedrowski | G02B 23/2476 385/11 |
| 2018/0132698 A1* | 5/2018 | Galstian | A61B 1/00016 |

FOREIGN PATENT DOCUMENTS

| | | | | |
|---|---|---|---|---|
| JP | H0915535 | * | 1/1997 | |
| JP | H11183809 A | * | 7/1999 | |
| JP | 2000338385 A | * | 12/2000 | |
| JP | 2008033060 A | * | 2/2008 | |
| JP | 4383005 B2 | * | 12/2009 | |
| JP | 2014-507856 A | | 3/2014 | |
| WO | WO-2007105767 A1 | * | 9/2007 | ........... G11B 7/1367 |
| WO | 2015/083162 A1 | | 6/2015 | |

OTHER PUBLICATIONS

International Search Report and Written Opinion dated Mar. 6, 2018 for PCT/EP2017/082914 filed on Dec. 14, 2017, 10 pages.

* cited by examiner

CAPTURING AN IMAGE OF A SCENE

CROSS-REFERENCE TO RELATED APPLICATIONS

The present application is based on PCT filing PCT/EP2017/082914, filed Dec. 14, 2017 which claims priority to EP 16204875.5 filed Dec. 16, 2016, the entire contents of each are incorporated herein by reference.

BACKGROUND

Field of the Disclosure

The present disclosure relates to a capturing an image of a scene.

Description of the Related Art

The "background" description provided herein is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present disclosure.

A problem with certain image capture devices such as those used in industrial instruments (such as industrial endoscopes) or medical instruments (such as medical endoscopes) is the limited depth of field at which high spatial frequencies can be obtained in order to capture a sufficiently sharp image. In order to improve the depth of field, the size of the aperture through which light travels to form the image to be captured can be reduced (increasing the so-called F number (F #) of the image capture device). This leads to a larger depth of field, but, in turn, reduces the resolution/in-focus sharpness (due to diffraction) and increases the noise of the captured image (due to there being less received light and thus a reduced signal to noise ratio). In other words, there is a trade off between having a larger depth of field and having greater in-focus sharpness and low noise images. Furthermore, as the form factor of such image capture devices is reduced (for example, to allow for smaller form factor endoscopes), this requiring image capture sensors with smaller pixel sizes, the problems of this approach are set to get worse. There is therefore a need to overcome this problem.

SUMMARY

The present disclosure provides an imaging device for use with an endoscope, the imaging device comprising: a lens arrangement operable to receive light from a scene captured by the endoscope and to form an image of the scene using the received light; an image sensor operable to capture the image of the scene formed by the lens arrangement; a birefringent device positioned along an optical path between the endoscope and the image sensor, wherein the birefringent device comprises birefringent material arranged in a plurality of concentric rings, and wherein the birefringent material of each of the concentric rings is configured such that the polarisation directions of an ordinary ray and an extraordinary ray of light from the scene which travels through the birefringent material are different for at least two of the plurality of concentric rings; and an image processor operable to process the captured image to generate an output image.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DESCRIPTION OF THE EMBODIMENTS

Referring now to the drawings, wherein like reference numerals designate identical or corresponding parts throughout the several views.

Figure 1:
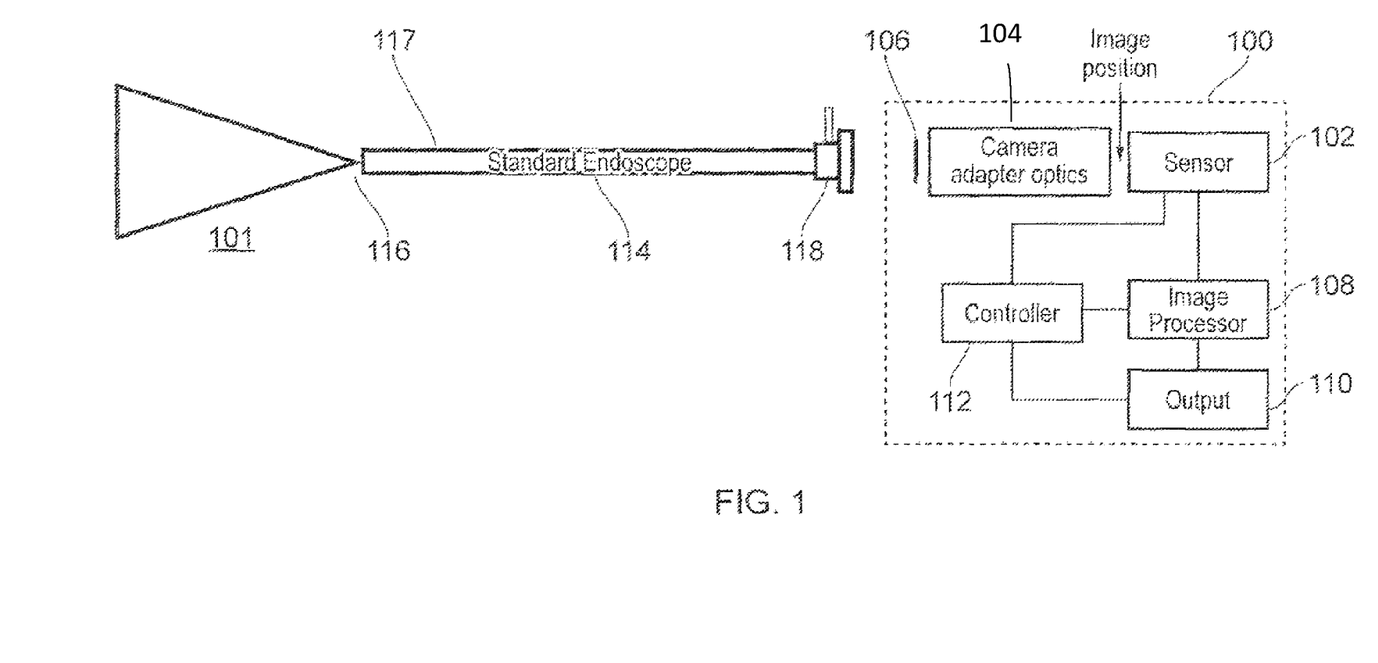
FIG. 1 schematically shows an optical device according to an embodiment of the present technique.

FIG. 1 shows an optical device 100 for capturing an image of a scene 101 according to an embodiment of the present technique. The optical device 100 comprises an image sensor 102 (such as a charged coupled device (CCD), complementary metal oxide semiconductor (CMOS) or Organic CMOS image sensor, for example), a birefringent device 106 (such as a phase mask or birefringent mask, for example), a lens arrangement 104 (this being an arrangement of one or more lenses and being camera adapter optics in this embodiment), an image processor 108 and an output 110. The operation of each of the sensor 102, image processor 108 and output 110 is controlled by a controller 112.

In operation, the lens arrangement 104 receives light from the scene and forms an image of the scene on the image sensor 102 using the received light. The image sensor then captures the image of the scene (that is, it captures the image of the scene as an electronic image). This electronic image is then processed by the image processor 108 and output for display and/or storage by the output 110.

The birefringent device 106 is positioned along the optical path between the scene and the image sensor 102. More specifically, the birefringent device 106 may be positioned along the optical path between the scene and the lens arrangement 104 or at a pupil plane of the lens arrangement 104. The birefringent device 106 comprises birefringent material arranged in a plurality of concentric rings. The birefringent material of each of the concentric rings is configured such that the polarisation directions of an ordinary ray and an extraordinary ray of light from the scene which travels through the birefringent material vary for each of the concentric rings of birefringent material (in particular, so that the polarisation directions of the ordinary ray and the extraordinary ray are different for at least two of the plurality of concentric rings). This is achieved by, for example, varying the direction of the optic axis of the birefringent material of each concentric ring so that the polarisation direction of the ordinary ray (and therefore the polarisation direction of the extraordinary ray, which is always perpendicular to that of the ordinary ray) is correspondingly varied. Birefringence in this context is discussed in, for example, published US patent application US 2012/0281280 A1. As will be explained, the use of a suitably configured birefringent device of this type results in the captured image of the scene exhibiting a constant blur level over a predetermined object distance range in the scene. This then allows the image processor 108 to apply suitable post-processing to the captured image in accordance with the constant blur level so as to remove the constant blur level from the captured image. An example of such post-processing is the application of a suitable inverse filter (such as an inverted in-focus point spread function when the constant blur level is the predetermined object distance range is defined by an in-focus point spread function). The constant blur level improves the effectiveness of the post-processing in removing blur from the captured image. In one example, the polarisation directions of the ordinary ray and the extraordinary ray change by 90° for each consecutive concentric ring in the birefringent device.

In the embodiment of FIG. 1, the light from the scene used to form the captured image is received from a medical instrument (in this example, a medical endoscope 114, such as a surgical endoscope). That is, the lens arrangement 104 receives light from the scene captured by the medical instrument and forms the image of the scene on the image sensor using this received light. It will be appreciated, however, that light from the scene may be received from any other type of instrument, as long as the light travels through the birefringent device 106 and is then focussed by the lens arrangement 104 onto the image sensor 102. An example of another type of instrument is an industrial instrument such as an industrial endoscope. In the example of FIG. 1, the instrument is a medical endoscope 114. Light from the scene enters an entrance pupil at a distal end 116 of the medical endoscope, travels down one or more optical elements 117 of the endoscope, and exits the endoscope through an exit pupil at the proximal end 118 of the endoscope. This light is then received by the lens arrangement 104 (after travelling through the birefringent device 106) and an image is formed on the image sensor 102.

Figure 2A:
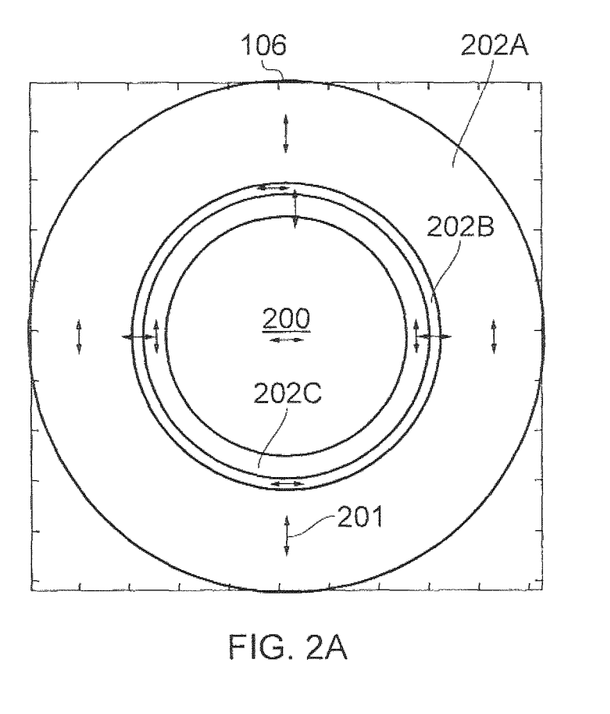
FIGS. 2A and 2B each schematically show a cross-section of an example birefringent device.
Figure 2B:
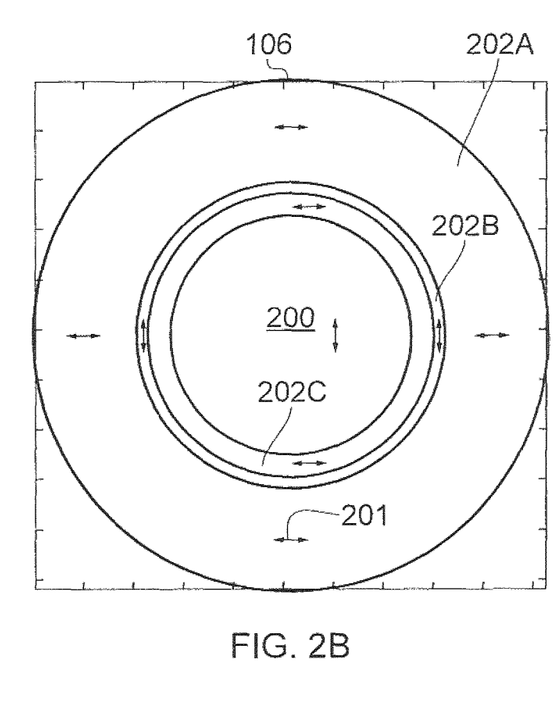

FIGS. 2A and 2B show a cross-section of an example birefringent device 106. Light from the scene travels through this cross section in order to reach the lens arrangement 104. In this example, the birefringent device 106 comprises birefringent material arranged in three concentric rings 202A, 202B and 202C. The birefringent device 106, in this example, also comprises a central circular portion 200 which is concentric with each of the concentric rings and which has a diameter sized such that it is within an inner diameter of each of the concentric rings (the inner diameter of each ring being the diameter of the smaller circle which forms one cross-sectional boundary of the ring and an outer diameter of each ring being the diameter of the larger circle which forms the other cross-sectional boundary of the ring). As previously mentioned, the birefringent material of each of the concentric rings is configured such that the polarisation directions of an ordinary ray and an extraordinary ray of light from the scene which travels through the birefringent material differ for at least two of the concentric rings of birefringent material. Two different examples of this are given, respectively, in FIGS. 2A and 2B, in which the arrows 201 illustrate the polarisation direction of the ordinary ray for each concentric ring (and for the central circular portion 200). It is seen here that the polarisation direction of the ordinary ray (and therefore of the extraordinary ray, whose polarisation direction is always perpendicular to that of the ordinary ray) for each consecutive concentric ring as one travels from the centre of the birefringent device to the outer edge of the birefringent device changes by 90°.

The birefringent performance (as determined by, for example, the width of each ring and the thickness of the birefringent material of each ring) is chosen in accordance with the desired depth of field extension, the optical properties of the optical device 100 (such as the optical properties of the lens arrangement 104, for example), the optical properties of any device (such as the cross-sectional diameter of the endoscope 114, for example) via which light from the scene is received by the optical device 100 and/or the distance of the birefringent device 106 relative to the lens arrangement 104 so that the captured image of the scene exhibits a constant blur level over a predetermined object distance range in the scene.

In the examples of FIGS. 2A and 2B, the polarisation direction of the ordinary ray changes by 90° for each consecutive concentric ring in the birefringent device 106. Thus, for example, in each of FIGS. 2A and 2B, concentric ring 202B has an ordinary ray polarisation direction which is at 90° to the ordinary ray polarisation direction of concentric ring 202A and concentric ring 202C, in turn, has an ordinary ray polarisation direction which is at 90° to the ordinary ray polarisation direction of concentric ring 202B. Furthermore, the central circular portion 200 has an ordinary ray polarisation direction which is at 90° to the ordinary ray polarisation direction of concentric ring 202C.

One or more of the cross-sectional width, cross-sectional position and thickness of each ring may also be chosen so as to help exhibit a constant blur level over the predetermined object distance. In one embodiment, the thickness of each ring is the same for all rings of the birefringent device. It is noted that the thickness of each ring refers to the dimension of the ring over which light travels between being incident on the birefringent device and being transmitted by the birefringent device. Thus, for example, in FIGS. 2A and 2B, the thickness of each ring refers to the dimension of each ring going into the page.

Figure 3:
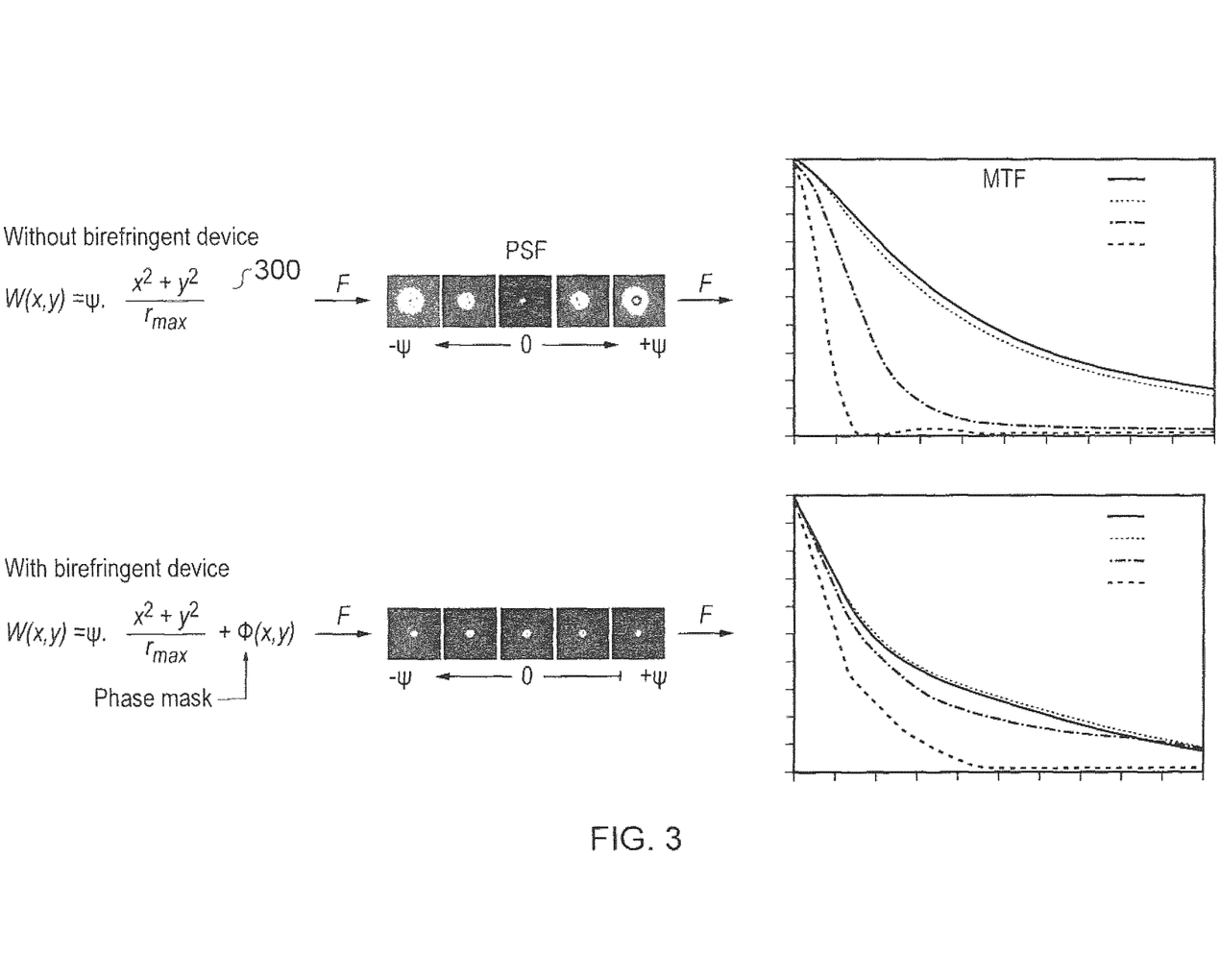
FIG. 3 schematically shows how a constant blur level in a captured image for different object distances is enabled by a birefringent device.

The constant blur level in the captured image for different object distances that is enabled by a birefringent device 106 of the type described is illustrated in FIG. 3. Here, it can be seen that, without the birefringent device 106, the blur level associated with a captured point in the scene (as measured by the point spread function (PSF) for that point) varies as a function of the object distance of that point in the scene over a predetermined distance range. On the other hand, when the system includes a suitable birefringent device 106 as described, the blur level associated with a captured point in the scene (as measured by the point spread function (PSF) for that point) remains constant as the object distance of that point in the scene is changed over the predetermined distance range. This is because, in effect, the addition of the birefringent device 106 introduces an additional term $\phi$ to the equation 300 for determining the PSF W of a captured point in the scene which results in the PSF W becoming constant. It is noted that the MTF graphs shown in FIG. 3 show the modulation (vertical axis) against spatial frequency (horizontal axis) for a single wavelength of light. Each line is representative of the MTF at a different object distance. For the example of FIG. 3, the birefringent device 106 used was a phase mask with aperture F/4, four concentric rings and a birefringent material with $\Delta n$ (that is, the difference between ordinary refractive index $n_o$ and extraordinary refractive index $n_e$)=0.054 at 530 nm wavelength. The birefringent material used was liquid crystal polymer (LCP).

FIGS. 4A-D and 5A-D also show the effect of using a birefringent device 106 on the MTF and PSF.

Figure 4A:
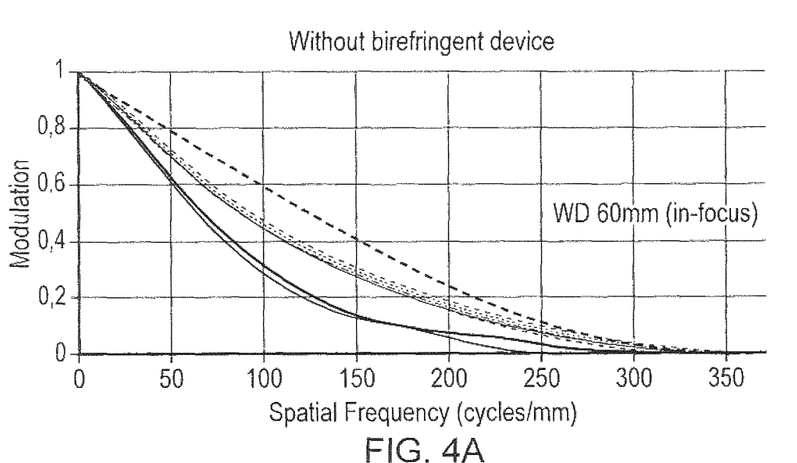
FIGS. 4A-D and 5A-D show an example the effect of using a birefringent device on the modular transfer function and point spread function.
Figure 4B:
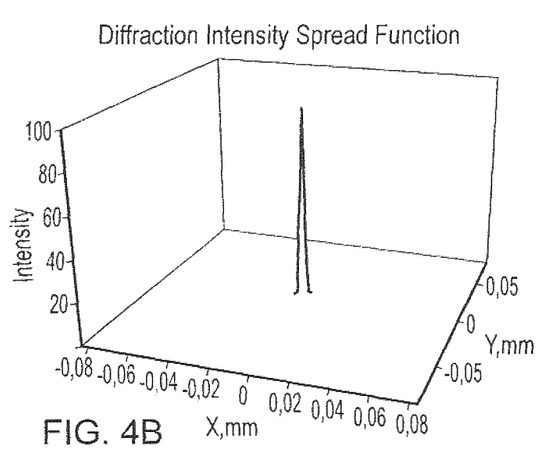
Figure 4C:
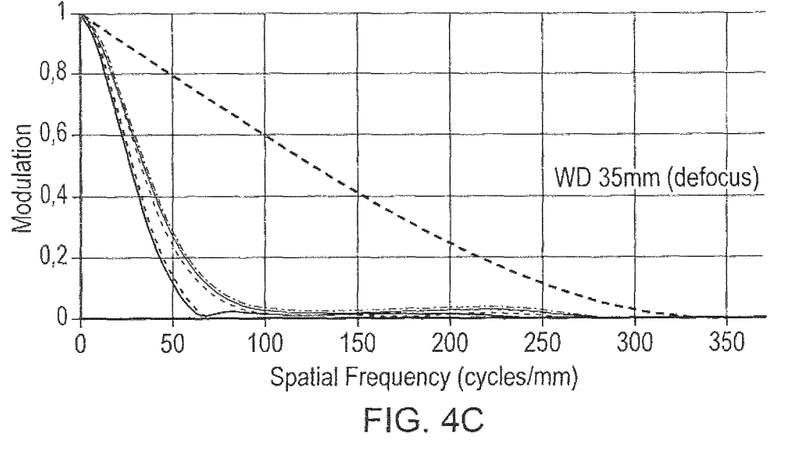
Figure 4D:
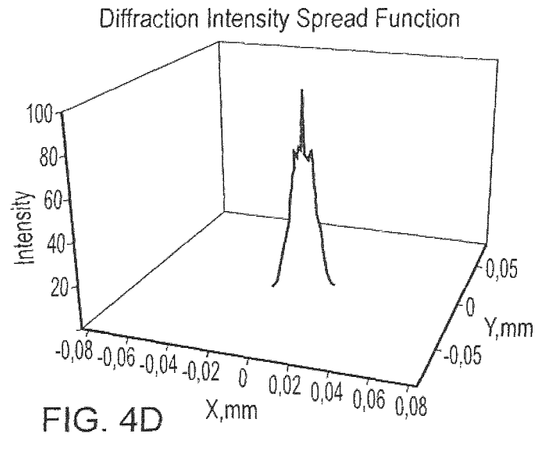
Figure 5A:
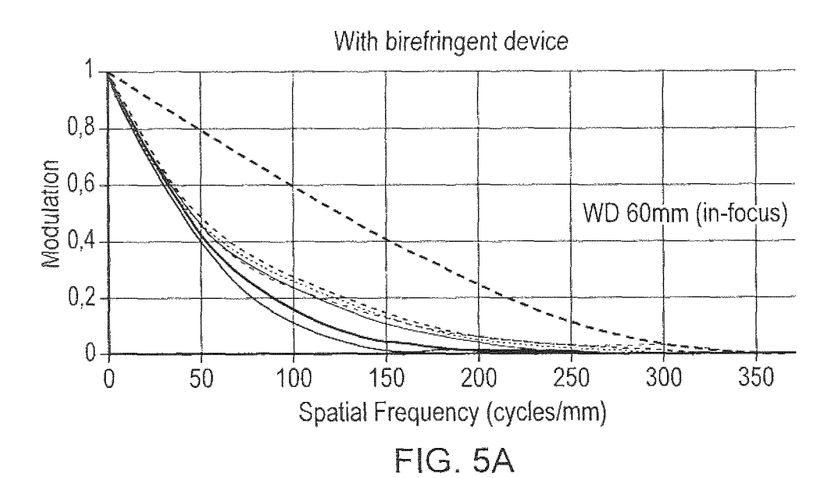
Figure 5B:
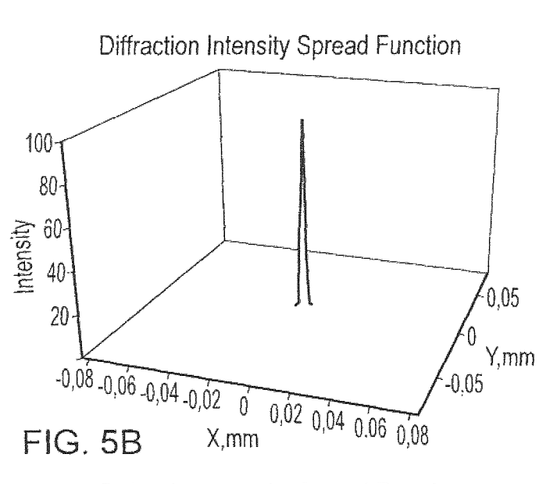
Figure 5C:
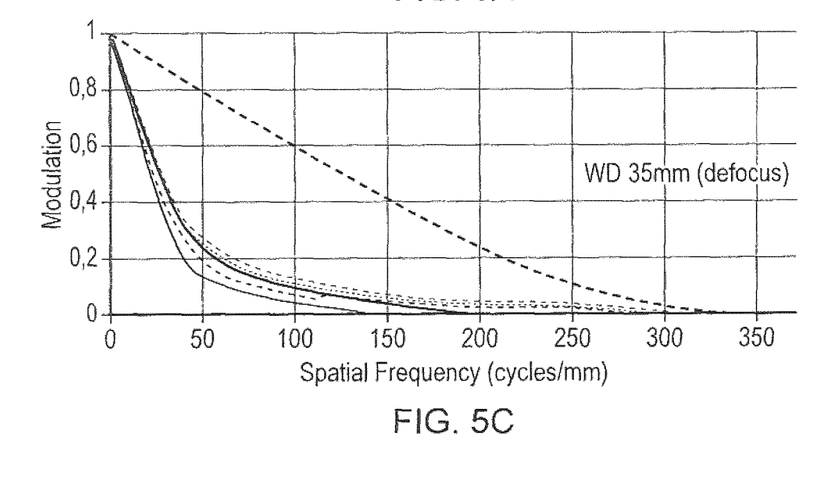
Figure 5D:
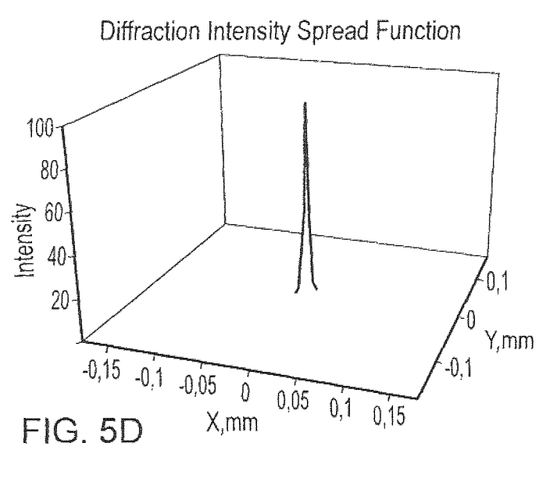

FIGS. 4A-D show the situation in which no birefringent device 106 is used. FIGS. 4A and 4C show the MTF for two different object distances (60 mm and 35 mm, respectively). Each line on the graphs of FIGS. 4A and 4C represents a different wavelength of visible light. Here, it can be seen that, when the position of a captured object in the scene is changed from the in-focus position (60 mm in this case, as shown in FIG. 4A) to an out-of-focus position (35 mm in this case, as shown in FIG. 4C), there is a significant change in the behaviour of the MTF for several of the wavelengths. Similarly, as shown in FIGS. 4B and 4D, it can be seen that, when the position of the captured object in the scene is changed from the in-focus position (60 mm) to the out-of-focus position (35 mm), there is a significant change in the behaviour of the diffraction intensity spread function (point spread function). Namely, there is a broadening of the blur diameter. This is indicative of the change in the blur level as the position of an object in the scene is varied when no birefringent device is used in the way as described.

FIGS. 5A-D show the situation in which a birefringent device 106 of the type described is used. FIGS. 5A and 5C again show the MTF for two different object distances. Each line on the graph represents a different wavelength of visible light. Here, it can be seen that, when the position of the captured object in the scene is changed from the in-focus position (60 mm) to the out-of-focus position (35 mm), the change in the behaviour of the MTF for each of the wavelengths is less significant. Similarly, as shown FIGS. 5B and 5D, it can be seen that, when the position of the captured object in the scene is changed from the in-focus position (60 mm) to the out-of-focus position (35 mm), there is a less significant change in the behaviour of the diffraction intensity spread function (point spread function). Namely, there is significantly less broadening of the blur diameter. This is indicative that the change in the level of blur as the position of an object in the scene is varied is alleviated when a birefringent device is used in the way as described, thus allowing the level of blur to be perceived as constant (even for captured objects at different object distances). In addition, higher spatial frequencies are still transmitted at the 35 mm defocus position with a lower contrast level compared to the situation in which no birefringent device 106 is used.

For the example of FIGS. 5A-D, the birefringent device 106 was a phase mask used with a 10 mm diameter endoscope with a 4 mm aperture diameter. The aperture number was F/5.9 and the phase mask had a 4 mm aperture diameter, 3 concentric rings, 1 μm material thickness and $\Delta n$=0.054 at 530 mm. The birefringent material used was LCP. This mask also had a central circular portion like the central circular portion 200 shown in FIGS. 2A and 2B, although the difference here was that the birefringent material of the central circular portion exhibited an ordinary ray polarisation direction which was at 45° to the ordinary ray polarisation directions of each of the concentric rings (rather than being at 0° or 90°, as is the case in FIGS. 2A and 2B). The diameter of the central circular portion was 2 mm. As will be explained, this enables a 10 mm diameter endoscope with a 4 mm aperture (from which light received should travel through the concentric rings of the mask in order to achieve a constant level of blur and to hence allow extended depth of field over a predetermined object distance range) to be substituted for a 4 mm diameter endoscope with a 2 mm aperture (which, due to its smaller diameter, already has a sufficient depth of field over the predetermined object distance range and which therefore does not need to be extended) without the need for the mask to be removed.

By having a constant level of blur (as defined by an in-focus point spread function, for example) at different object distances through the use of the described birefringent device 106, post processing to remove the blur is made easier. For example, a single inverse filter (for example, an inverse of the in-focus point spread function) may be applied to the captured image by the image processor 108 in order remove the blur and to thus form an image with a larger perceived depth of field. The perceived depth of field will be extended such that all captured objects in the scene for which the blur is constant by the use of the birefringent device 106 will appear to be in focus. A larger aperture (lower F #) may therefore be used (thus allowing increased in-focus sharpness (resolution) of the captured image and reduced image noise) whilst the problem of reduced depth of field resulting from using a larger aperture is alleviated.

It is noted that the term "constant blur" resulting from the use of the birefringent device 106 should be taken to mean that the variation in the blur level for different object distances of the captured image is sufficiently small over the user's desired object distance range such that, once suitable post processing to remove the blur is applied to the image by the image processor 108, the perceived extension to the depth of field is acceptable to the user. The perceived extension to the depth of field will be acceptable to the user if, for example, all objects captured in the image within the object distance of interest are perceived by the user to be sufficiently in focus. A suitably extended depth of field may be obtained by, for example, determining a threshold representative of the amount of change in the MTF and/or PSF between two predetermined object distances and only accepting the blur in the captured image to be sufficiently "constant" when the amount of change in the MTF and/or PSF is lower than the determined threshold.

Figure 6:
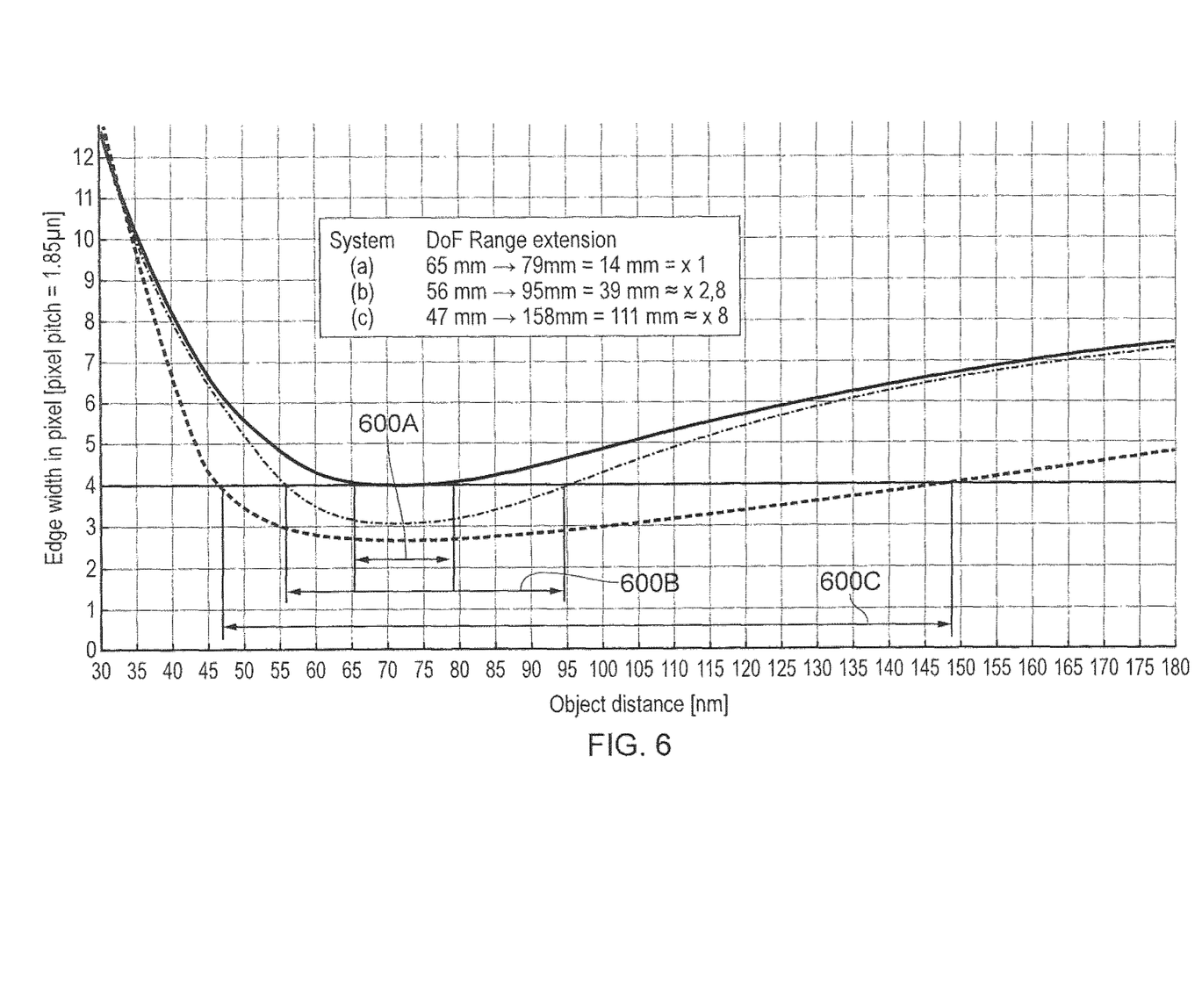
FIG. 6 shows an example of a comparison of the depth of field of a captured image when (a) no birefringent device or inverse filter is used, (b) no birefringent device is used but an inverse filter is used and (c) both a birefringent device and an inverse filter are used.

FIG. 6 is a specific example showing a comparison of the depth of field of a captured image of an endoscope system like that shown in FIG. 1 when (a) no birefringent device or inverse filter is used, (b) no birefringent device is used but an inverse filter is used and (c) both a birefringent device and an inverse filter are used. The birefringent device 106 used in this case was a phase mask with the same characteristics as the phase mask used to generate FIGS. 5A-D. In this case, it was determined that a blur width of a black and white edge in the captured image of 4 pixels (pixel pitch=1.85 μm) was sufficient for an object to be deemed sufficiently in focus and to thus be within the perceived depth of field. It can be seen in FIG. 6 that for situation (a) (when no birefringent device or inverse filter was used), the depth of field (indicated by arrows 600A) was 14 mm. For situation (b) (when no birefringent device was used but an inverse filter was used), the depth of field (indicated by arrows 600B) was 39 mm (approximately 2.8× the depth of field of situation (a)). For situation (c) (when both a birefringent device and an inverse filter were used), the depth of field (indicated by arrows 600C) was 158 mm (approximately 8× the depth of field of situation (a)). The effectiveness of the present technique in extending the depth of field is thus illustrated by FIG. 6.

Table 1 shows the characteristics of a particular birefringent device 106 according to the present technique. The birefringent device is a 4 mm aperture diameter phase mask (making it suitable for use with a 10 mm diameter endoscope with a 4 mm aperture diameter) with three concentric birefringent rings and a central circular portion. The central circular portion and three concentric rings each respectively apply birefringence such that the polarisation direction of the ordinary ray differs by 90° for the central circular portion and each consecutive ring when moving from the centre of the mask to its outer edge. The birefringent device described in Table 1 had a thickness of approximately 3 µm and $\Delta n=0.054$ at 530 nm. The birefringent material used was LCP. This birefringent device was found to be particularly effective in combination with suitable post processing for providing a greater depth of field in images captured using a small F #.

TABLE 1

|  | Central Circular Portion | ring1 | ring2 | ring3 |
| --- | --- | --- | --- | --- |
| Relative (to ring3 radius) | 0.47 | 0.56 | 0.60 | 1 |
| Absolute distance from center in mm | 0.96 | 1.15 | 1.23 | 2.05 |
| Ring width in mm |  | 0.19 | 0.09 | 0.82 |

It is noted that the "relative (to ring 3 radius)" and "absolute distance from the centre" values are measured with respect to the outer radius of the appropriate ring. It will also be appreciated that the characteristics shown in Table 1 are merely example characteristics of a birefringent device which may be used with the present technique, and that the skilled person may vary these characteristics in accordance with the properties of the system (such as an endoscope) with which the birefringent device is to be used.

In general, it has been found that the present technique is particularly effective when used with endoscopes with an outer diameter of between 4-10 mm (and aperture 2-4 mm) and with any length of telescopic rod (in particular, 150-350 mm). The present technique is also particularly effective when used with an endoscope focal length of 2-5 mm, a F/# of F/2-F/8, an image height at sensor of 6-9 mm and a sensor pixel pitch of 1-2 µm.

It is noted that, in general, using a birefringent device with a central circular portion which applies birefringence with an ordinary ray polarisation direction different to that of each of the concentric birefringent rings (such as at 45° to the ordinary ray polarisation directions of each of the concentric rings, as was the case with the birefringent device used for generating FIGS. 5A-D and 6 and Table 1) allows the birefringent device to remain in place as part of the optical device 100 even when the instrument (such as endoscope 114) through which light enters the optical device 100 is changed. For example, the central aperture allows a larger diameter endoscope (such as a 10 mm endoscope with a 4 mm aperture, for which extended depth of field is required for a particular application) to be changed for a smaller diameter endoscope (such as 4 mm endoscope with a 2 mm aperture, for which extended depth of field is not required for that particular application), and vice versa, without the need to remove or change the birefringent device. This reduces the time required for changing the endoscope. Such time saving is particularly beneficial for medical endoscopes, in particular, surgical endoscopes, since it allows the surgery time to be reduced. It is noted that the larger and smaller diameter endoscopes may have any suitable respective diameters for the specific application at hand. In each case, the characteristics of the birefringent device can be chosen such that the blur of the large diameter endoscope over the predetermined object distance range is affected by the birefringent device but the blur of the small diameter endoscope over the predetermined object distance range is not affected by the birefringent device. This is useful when the smaller aperture of such endoscopes means that the depth of field is already sufficiently large, and thus it is not necessary for the images captured using such endoscopes to be altered by the birefringent device or image processor 108. It is noted that refraining from such unnecessary image alteration helps to maintain the quality of the images captured using such small aperture endoscopes.

Figure 7A:
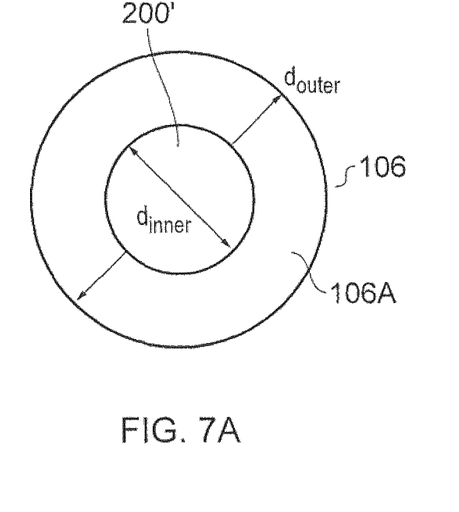
FIGS. 7A and 7B show a comparison of a birefringent device with and without a central aperture.
Figure 7B:
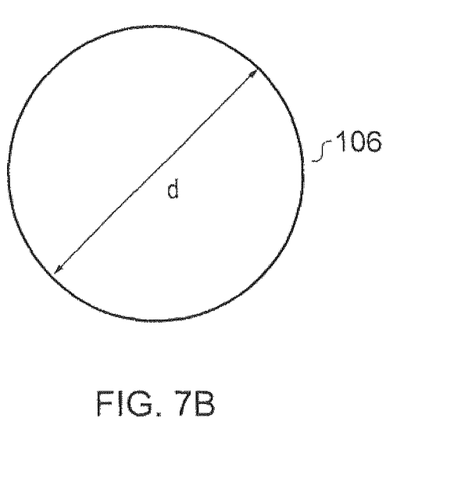

For completeness, a schematic diagram of a birefringent device 106 with and without a central circular portion 200' with an ordinary ray polarisation direction different to that of each of the concentric birefringent rings is shown in FIGS. 7A and 7B. FIG. 7A shows a birefringent device 106 with such a central circular portion 200'. The diameter $d_{inner}$ of the central aperture is set such that light captured by an endoscope with an aperture diameter less than or equal to $d_{inner}$ is masked by the central circular portion 200' but not the plurality of concentric rings. On the other hand, the diameter $d_{outer}$ of the birefringent device is set such that light captured by larger aperture diameter endoscopes is masked by both the central circular portion 200' and the plurality of concentric rings (the plurality of concentric rings providing the constant blur level so as to allow extended depth of field, as previously discussed). In one embodiment (such as that used for generating FIGS. 5A-D and 6), $d_{inner}=2$ mm and $d_{outer}=4$ mm, thus providing extended depth of field for 10 mm diameter endoscopes (with a 4 mm aperture) but not for 4 mm diameter endoscopes (with a 2 mm aperture). It is noted that, in FIG. 7A, the concentric birefringent rings are present only in the portion 106A of the birefringent device 106 which is defined between the diameters $d_{inner}$ and $d_{outer}$. FIG. 7B shows a birefringent device 106 without a central circular portion 200' with an ordinary ray polarisation direction different to that of each of the concentric birefringent rings. In this case, concentric birefringent rings may be present over the entire diameter d of the birefringent device, and a central circular portion 200 like that shown in FIGS. 2A and 2B (in which the ordinary ray polarisation direction is at 0° or 90° to that of each of the concentric rings) will be present. The birefringent device of FIG. 7B does not allow a distinction to be made between larger diameter endoscopes and smaller diameter endoscopes in the same way as made by the birefringent device of FIG. 7A. The birefringent device of FIG. 7B therefore does not allow extended depth of field to be applied selectively to different diameter endoscopes (as is possible with the birefringent device of FIG. 7A).

Figure 8:
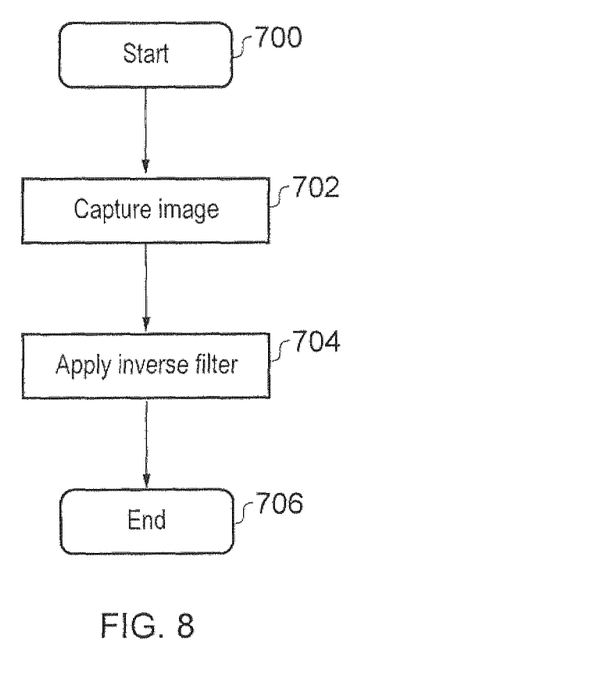
FIG. 8 shows a flow chart schematically illustrating a process according to an embodiment of the present technique.

Figure shows a flow chart schematically illustrating a process according to an embodiment of the present technique. The process starts at step 700. At step 702, the controller 112 controls the image sensor 102 to capture an image of the scene. The birefringent device 106 is positioned along an optical path between the scene and the image sensor. The birefringent device comprises birefringent material arranged in a plurality of concentric rings. The birefringent material of each of the concentric rings is configured such that the polarisation directions of an ordinary ray and an extraordinary ray of light from the scene which travels through the birefringent material are different for at least two of the concentric rings. This results in the captured image of the scene exhibiting a constant level of blur over a predetermined object distance range in the scene. The blur may be represented by an in-focus point spread function. In one embodiment, the polarisation directions of the ordinary ray and the extraordinary ray differ by 90° for the at least two of the plurality of concentric rings. At step 704, the controller 112 controls the image processor 108 to process the capture image to generate an output image. This processing removes the constant level of blur from the captured image. The processing may comprise applying an inverse of the in-focus point spread function to the captured image, for example. The process then ends at step 706.

Various embodiments of the present disclosure are defined by the following numbered clauses:

1. An imaging device for use with an endoscope, the imaging device comprising:
    a lens arrangement operable to receive light from a scene captured by the endoscope and to form an image of the scene using the received light;
    an image sensor operable to capture the image of the scene formed by the lens arrangement;
    a birefringent device positioned along an optical path between the endoscope and the image sensor, wherein the birefringent device comprises birefringent material arranged in a plurality of concentric rings, and wherein the birefringent material of each of the concentric rings is configured such that the polarisation directions of an ordinary ray and an extraordinary ray of light from the scene which travels through the birefringent material are different for at least two of the plurality of concentric rings; and
    an image processor operable to process the captured image to generate an output image.
2. The imaging device according to clause 1, wherein the polarisation directions of the ordinary ray and the extraordinary ray differ by 90° for the at least two of the plurality of concentric rings.
3. The imaging device according to clause 2, wherein the birefringent device comprises a central circular portion which is concentric with each of the concentric rings and which has a diameter such that the central circular portion is within an inner diameter of each of the concentric rings, wherein a birefringent material of the central circular portion is configured such that the polarisation directions of the ordinary ray and the extraordinary ray for the central circular portion are different to the polarisation directions of the ordinary ray and the extraordinary ray for each of the plurality of concentric rings.
4. The imaging device according to clause 3, wherein the polarisation directions of the ordinary ray and the extraordinary ray for the central circular portion differ by 45° to the polarisation directions of the ordinary ray and the extraordinary ray for each of the plurality of concentric rings.
5. The imaging device according to clause 3 or 4, wherein:
    an inner diameter and outer diameter of each of the plurality of concentric rings and a diameter of the central circular portion are configured such that:
    light captured by a first endoscope with a larger diameter is masked by the central circular portion and the plurality of concentric rings; and
    light captured by a second endoscope with a smaller diameter is masked by the central circular portion only.
6. The imaging device according to any preceding clause, wherein the birefringent device is positioned along an optical path between the endoscope and the lens arrangement.
7. The imaging device according to any one of clauses 1 to 5, wherein the birefringent device is positioned at a pupil plane of the lens arrangement.
8. The imaging device according to any preceding clause, wherein the image processor is operable to apply processing to the captured image so as to remove blur from the captured image, the blur being constant over a predetermined object distance range in the captured image in accordance with one or more characteristics of the birefringent device.
9. The imaging device according to clause 8, wherein the blur is defined by an in-focus point spread function and the processing comprises applying an inverse of the in-focus point spread function to the captured image.
10. The imaging device according to any preceding clause, wherein the endoscope is a medical endoscope.
11. A system comprising an optical device according to any preceding clause and an endoscope configured to captured light from the scene for use by the lens arrangement of the imaging device in forming an image of the scene on the image sensor of the imaging device.
12. A birefringent device for use with an imaging device according to any preceding clause, the birefringent device being positionable along an optical path between an endoscope for capturing light from a scene and an image sensor of the imaging device on which an image of the scene is formed using the captured light, wherein the birefringent device comprises birefringent material arranged in a plurality of concentric rings, and wherein the birefringent material of each of the concentric rings is configured such that the polarisation directions of an ordinary ray and an extraordinary ray of light from the scene which travels through the birefringent material are different for at least two of the plurality of concentric rings; wherein:
    the polarisation directions of the ordinary ray and the extraordinary ray differ by 90° for the at least two of the plurality of concentric rings; and
    the birefringent device comprises a central circular portion which is concentric with each of the concentric rings and which has a diameter such that the central circular portion is within an inner diameter of each of the concentric rings, wherein the birefringent material of the central circular portion is configured such that the polarisation directions of the ordinary ray and the extraordinary ray for the central circular portion are different to the directions of the polarisation directions of the ordinary ray and the extraordinary ray for each of the plurality of concentric rings.
13. A birefringent device according to clause 12, wherein the polarisation directions of the ordinary ray and the extraordinary ray for the central circular portion differ by 45° to the polarisation directions of the ordinary ray and the extraordinary ray for each of the plurality of concentric rings.
14. A birefringent device according to clause 10 or 11, wherein:
    an inner diameter and outer diameter of each of the plurality of concentric rings and a diameter of the central circular portion are configured such that:
    light captured by a first endoscope with a larger diameter is masked by the central circular portion and the plurality of concentric rings; and
    light captured by a second endoscope with a smaller diameter is masked by the central circular portion only.
15. A method of capturing an image of a scene, the method comprising:

capturing an image of the scene using an image sensor, the image of the scene being formed at the image sensor by a lens arrangement using light from the scene captured by an endoscope, wherein a birefringent device is positioned along an optical path between the endoscope and the image sensor, wherein the birefringent device comprises birefringent material arranged in a plurality of concentric rings, and wherein the birefringent material of each of the concentric rings is configured such that the polarisation directions of an ordinary ray and an extraordinary ray of light from the scene which travels through the birefringent material are different for at least two of the plurality of concentric rings; and processing the captured image to generate an output image.

16. A recording medium storing a computer program for controlling a computer to perform a method according to clause 15.

Obviously, numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

The invention claimed is:

1. An imaging device for use with an endoscope, the imaging device comprising:
a lens arrangement operable to receive light from a scene captured by the endoscope and to form an image of the scene using the received light;
an image sensor operable to capture the image of the scene formed by the lens arrangement;
a birefringent device positioned along an optical path between the endoscope and the image sensor, wherein the birefringent device includes:
a birefringent material arranged in a plurality of concentric rings, and wherein the birefringent material of each of the plurality of concentric rings is configured such that polarization directions of an ordinary ray and an extraordinary ray of light from the scene which travel through the birefringent material are different for at least two of the plurality of concentric rings;
a central circular portion which is concentric with each of the plurality of concentric rings and which has a diameter such that the central circular portion is within an inner diameter of each of the plurality of concentric rings, wherein a birefringent material of the central circular portion is configured such that the polarization directions of the ordinary ray and the extraordinary ray for the central circular portion are different to the polarization directions of the ordinary ray and the extraordinary ray for each of the plurality of concentric rings, wherein an inner diameter and outer diameter of each of the plurality of concentric rings and a diameter of the central circular portion are configured for use with a first endoscope with a larger diameter and a second endoscope with a smaller diameter such that:
light from the first endoscope is incident on the central circular portion and the plurality of concentric rings; and
light from the second endoscope is incident on only the central circular portion; and
an image processor operable to process the captured image to generate an output image.

2. The imaging device according to claim 1, wherein the polarization directions of the ordinary ray and the extraordinary ray differ by 90° for the at least two of the plurality of concentric rings.

3. The imaging device according to claim 1, wherein the polarization directions of the ordinary ray and the extraordinary ray for the central circular portion differ by 45° to the polarization directions of the ordinary ray and the extraordinary ray for each of the plurality of concentric rings.

4. The imaging device according to claim 1, wherein the birefringent device is positioned along an optical path between the endoscope and the lens arrangement.

5. The imaging device according to claim 1, wherein the birefringent device is positioned at a pupil plane of the lens arrangement.

6. The imaging device according to claim 1, wherein the image processor is operable to apply processing to the captured image so as to remove blur from the captured image, the blur being constant over a predetermined object distance range in the captured image in accordance with one or more characteristics of the birefringent device.

7. The imaging device according to claim 6, wherein the blur is defined by an in-focus point spread function and the processing comprises applying an inverse of the in-focus point spread function to the captured image.

8. The imaging device according to claim 1, wherein the endoscope is a medical endoscope.

9. A system, comprising:
an optical device according to claim 1, and
an endoscope configured to captured light from the scene for use by the lens arrangement of the imaging device in forming an image of the scene on the image sensor of the imaging device.

10. A birefringent device for use with an imaging device according to claim 1, the birefringent device being positionable along an optical path between an endoscope for capturing light from a scene and an image sensor of the imaging device on which an image of the scene is formed using the captured light, wherein the birefringent device comprises birefringent material arranged in a plurality of concentric rings, and wherein the birefringent material of each of the concentric rings is configured such that polarization directions of an ordinary ray and an extraordinary ray of light from the scene which travels through the birefringent material are different for at least two of the plurality of concentric rings; wherein:
the polarization directions of the ordinary ray and the extraordinary ray differ by 90° for the at least two of the plurality of concentric rings; and
the birefringent device comprises a central circular portion which is concentric with each of the concentric rings and which has a diameter such that the central circular portion is within an inner diameter of each of the concentric rings, wherein the birefringent material of the central circular portion is configured such that the polarization directions of the ordinary ray and the extraordinary ray for the central circular portion are different to the directions of the polarization directions of the ordinary ray and the extraordinary ray for each of the plurality of concentric rings, wherein an inner diameter and outer diameter of each of the plurality of concentric rings and a diameter of the central circular portion are configured for use with a first endoscope with a larger diameter and a second endoscope with a smaller diameter such that:
light from the first endoscope is incident on the central circular portion and the plurality of concentric rings; and
light from the second endoscope is incident on only the central circular portion.

11. A birefringent device according to claim 10, wherein the polarization directions of the ordinary ray and the extraordinary ray for the central circular portion differ by 45° to the polarization directions of the ordinary ray and the extraordinary ray for each of the plurality of concentric rings.

12. A method of capturing an image of a scene, the method comprising: capturing an image of the scene using an image sensor, the image of the scene being formed at the image sensor by a lens arrangement using light from the scene captured by an endoscope, wherein a birefringent device is positioned along an optical path between the endoscope and the image sensor, wherein the birefringent device includes birefringent material arranged in a plurality of concentric rings, and wherein the birefringent material of each of the concentric rings is configured such that polarization directions of an ordinary ray and an extraordinary ray of light from the scene which travels through the birefringent material are different for at least two of the plurality of concentric rings, and a central circular portion which is concentric with each of the plurality of concentric rings and which has a diameter such that the central circular portion is within an inner diameter of each of the plurality of concentric rings, wherein a birefringent material of the central circular portion is configured such that the polarization directions of the ordinary ray and the extraordinary ray for the central circular portion are different to the polarization directions of the ordinary ray and the extraordinary ray for each of the plurality of concentric rings, wherein an inner diameter and outer diameter of each of the plurality of concentric rings and a diameter of the central circular portion are configured for use with a first endoscope with a larger diameter and a second endoscope with a smaller diameter such that: light from the first endoscope is incident on the central circular portion and the plurality of concentric rings; and light from the second endoscope is incident on only the central circular portion; and processing the captured image to generate an output image.

13. A non-transitory recording medium storing a computer program for controlling a computer to perform a method according to claim 12.

14. An imaging device for use with an endoscope, the imaging device comprising:
a lens arrangement operable to receive light from a scene captured by the endoscope and to form an image of the scene using the received light;
an image sensor operable to capture the image of the scene formed by the lens arrangement; and
a birefringent device positioned along an optical path between the endoscope and the image sensor, wherein the birefringent device includes:
a birefringent material arranged in a plurality of concentric rings around a central circular region, and wherein the birefringent material of each of the plurality of concentric rings is configured such that polarization directions of an ordinary ray and an extraordinary ray of light from the scene which travel through the birefringent material are different for at least two of the plurality of concentric rings, wherein the plurality of concentric rings includes a first ring closest to the central circular region and a second ring, wherein a first width of the first ring is greater than a second width of the second ring,
the first and second rings and a diameter of the central circular region are configured for use with a first endoscope with a larger diameter and a second endoscope with a smaller diameter such that:
light from the first endoscope is incident on the central circular region and the first and second rings; and
light from the second endoscope is incident on only the central circular region.

15. The imaging device according to claim 14, wherein a width and thickness of the birefringent material of the first ring and the second ring are set in accordance with a desired depth of field extension.

16. The imaging device according to claim 14, wherein the plurality of concentric rings further includes a third ring, and a first difference in radius between the first ring and the second ring is different than a second difference in radius between the second ring and the third ring.

17. The imaging device according to claim 16, wherein the first difference is less than the second difference.

* * * * *